Aug. 3, 1965 G. VERBEEK Plant Pat. 2,546
ROSE PLANT
Filed April 27, 1964
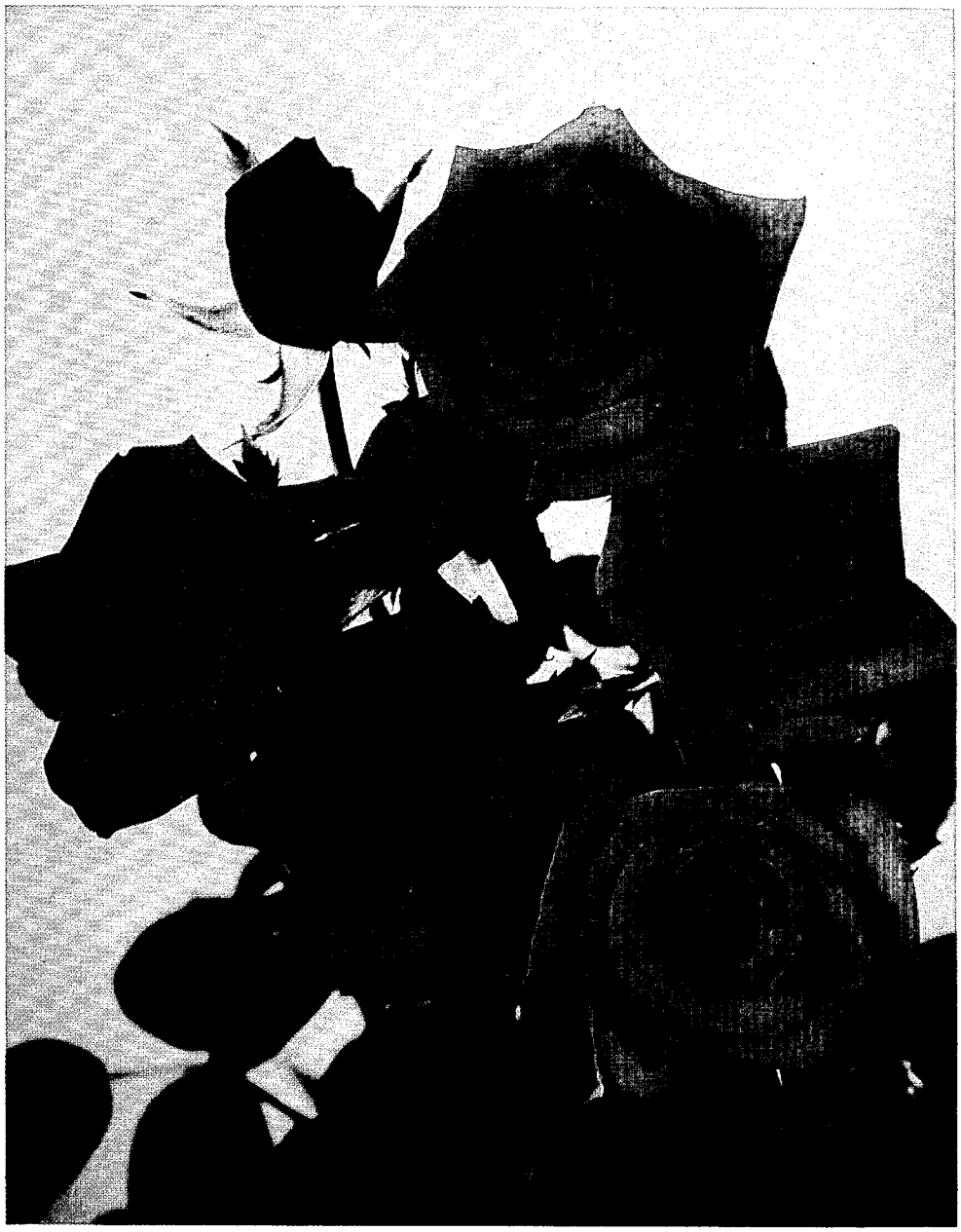
Inventor
Gysbert Verbeek
By: Robb & Robb
Attorneys.

United States Patent Office

Plant Pat. 2,546
Patented Aug. 3, 1965

2,546
ROSE PLANT

Gysbert Verbeek, Aalsmeer, Netherlands, assignor to Carlton Rose Nurseries, Carlton, Oreg., a corporation of Oregon Filed Apr. 27, 1964, Ser. No. 363,033
1 Claim. (Cl. Pit.—20)

The present invention relates to a new and distinct variety of rose plant of the hybrid tea class, which was originated by me by crossing the variety known as "Poinsettia" (unpatented) with an unnamed and unpatented seedling of "Baccara" (U.S. Plant Patent No. 1367) × an unnamed and unpatented seedling of unidentified parentage.

As the result of this breeding, I have produced a new rose variety which is distinguished from its parents and from all other varieties of its class of which I am aware, and which is particularly characterized as to novelty by the following unique combination of outstanding features:

(1) Glossy green, disease resistant foliage;
(2) Abundant flower production;
(3) Well-formed blooms of good longevity; and
(4) A distinctive and atractive general tonality of the flowers corresponding to cherry color.

Asexual reproduction of my new variety by grafting, as performed by me at Aalsmeer, Holland, shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of my new variety, with color terminology in accordance with the Horticultural Colour Chart issued by the British Colour Council in collaboration with The Royal Horticultural Society, except where general color terms of ordinary dictionary significance are obvious.

Type: Hardy; greenhouse; seedling; for cut flowers.
Class: Hybrid tea.
Breeding: Seedling.
*Seed parent.*—"Poinsettia."
*Pollen parent.*—An unnamed seedling of "Baccara" × an unnamed seedling of unidentified parentage.
Propagation: Holds its distinguishing characteristics through succeeding propagations by grafting.

*Flower*

Locality where grown and observed: Aalsmeer, Holland.
Continuity: Continuous.
Fragrance: Moderate.
Flowers borne: Several to stem; in regular flat clusters; on strong, medium long stems.
Quantity of bloom: Free, both outdoors and in greenhouse.
Bud:
*Peduncle.*—Upright; thorny; medium caliper; stiff. Color—green.
*Before calyx breaks.*—Size—medium. Form—oval; with a conspicuous neck; without foliaceous appendages on the surface of the bud. Color—violet-red.
*As calyx breaks.*—Size—medium. Color—violet-red.
*As first petal opens.*—Size—medium. Form—ovoid.

Color—outside: Currant Red, Plate 821/1; inside: Cardinal Red, Plate 822/3.
*Opening.*—Opens up well.
Bloom:
*Size (when fully open).*—Large; from 3 inches to 4 inches.
*Petalage.*—Double; from 44 to 62 petals; arranged regularly.
*Form.*—Full at first, becoming flat; petals at first tightly rolled outward, but later becoming flat and rolled outward at maturity.
Petals:
*Texture.*—Thick. Appearance—inside: satiny; outside: satiny.
*Shape.*—Outside—scalloped. Inside—scalloped.

This description of a newly opened flower was made from a rose grown outdoors in July and August at Aalsmeer, Holland:

Color:
*Outer petal.*—Outside surface—Cardinal Red, Plate 822/3. Inside surface—Currant Red, Plate 821/1.
*Intermediate petal.*—Outside surface—Turkey Red, Plate 721/1. Inside surface—Turkey Red, Plate 721/1.
*Inner petal.*—Outside surface—Turkey Red, Plate 721/1. Inside surface—Turkey Red, Plate 721.

This description was made from a rose that was open for three days outdoors in the month of August at Aalsmeer, Holland:

Color:
*Outer petal.*—Outside surface—Rose Red, Plate 724/2. Inside surface—Cherry, Plate 722/2.
*Intermediate petal.*—Outside surface—Rose Red, Plate 724/1. Inside surface—Rose Red, Plate 724.
*Inner petal.*—Outside surface—Cherry, Plate 722/1. Inside surface—Cherry, Plate 722/1.
General color effect:
*Newly opened flower.*—Currant Red.
*Three days open.*—Cherry.
Behavior: Drop off cleanly.
Flower longevity:
*On bush in garden.*—5 days in August and September.
*Cut roses grown in greenhouse and kept at living room temperatures.*—5 days in August and September.
*Cut roses grown outdoors and kept at living room temperatures.*—5 days in August and September.

*Reproductive organs*

Stamens: From 85–115 in number; regularly arranged.
*Color.*—Chinese Yellow, Plate 606.
Filaments: Medium length.
*Color.*—Yellow, Plate 07/1.
Anthers: Medium large; all open at once.
*Color.*—Yellow.
Pollen: Moderate abundant.
*Color.*—Gold.
Pistils: From 80–85 in number; irregularly arranged.
*Color.*—Amber Yellow, Plate 505.
Styles: Thin; bunched; irregularly arranged.
Stigma: Color—Yellow.
Ovaries: Some protruding from calyx.
Hips: Pear-shaped; very smooth; thin walls.
Sepals: Permanent; long.
*Color.*—Green.
Seeds: Moderate number; medium size.

*Plant*

Foliage:

*Leaves.*—Compound of 5–7 leaflets; normal quantity; moderately large; heavy; glossy.

*Leaflets.*—Shape—oval. Base—rounded. Margin—simply serrate.

*Color.*—Mature—upper surface: Glossy Dark Green; under surface: lighter green. Young—upper surface: Glossy Red; under surface: reddish.

*Rachis (the supporting stem of the compound leaf).*—Medium caliper. Upper side—hairy. Under side—moderately prickly.

*Stipules.*—Medium length; narrow; ⅔ part grown together with leaf stalk.

Foliage: Disease resistance—very good resistance to mildew and blackspot, as determined by comparison with other varieties grown under the same cultural conditions at Aalsmeer, Holland.

Growth:

*Habit.*—Bush.

*Growth.*—Free; heavy.

*Canes.*—Heavy.

*Main stems.*—Color—Green. Thorns—moderate number; length to 9 mm. Color: Reddish. Prickles: none. Hairs: none.

*Branches.*—Color—Green, but often somewhat purple. Thorns—several; medium length; hooked downwards; with round base. Prickles: none. Hairs: none.

*New shoots.*—Color—Purple-Brown. Thorns—several; medium length; hooked downwards; with round base. Prickles: none. Hairs: none.

I claim:

A new and distinct variety of rose plant of the hybrid tea class, substantially as herein shown and described, characterized particularly as to novelty by the unique combination of glossy Green, disease resistant foliage, abundant flower production, well-formed blooms of good longevity, and a distinctive and attractive general tonality of the flowers corresponding to Cherry color.

No references cited.

ABRAHAM G. STONE, *Primary Examiner.*